United States Patent [19]

Jung

[11] Patent Number: 5,139,782

[45] Date of Patent: Aug. 18, 1992

[54] FACIAL CLEANSING MINERAL COMPOSITIONS

[75] Inventor: Mary L. Jung, Millwood, N.Y.

[73] Assignee: UOP, Des Plaines, Ill.

[21] Appl. No.: 812,150

[22] Filed: Dec. 23, 1991

[51] Int. Cl.$^5$ .............................................. A61K 7/00
[52] U.S. Cl. .................................. 424/401; 424/683; 424/684; 514/844
[58] Field of Search ...................... 424/401, 683, 684; 514/844

[56] References Cited

U.S. PATENT DOCUMENTS

| | | | |
|---|---|---|---|
| 4,014,995 | 3/1977 | Juliano et al. | 424/70 |
| 4,122,192 | 10/1978 | Fellows | 514/705 |
| 4,735,802 | 4/1988 | Le | 424/154 |
| 4,847,078 | 8/1989 | Sheppard et al. | 514/777 |
| 4,965,071 | 10/1990 | Kawan | 424/401 |

OTHER PUBLICATIONS

U.S. application Ser. No. 600,782, filed Oct. 22, 1990; M. C. Tsoucalas.

Primary Examiner—Thurman K. Page
Assistant Examiner—Amy Hulina
Attorney, Agent, or Firm—Thomas K. McBride; Richard G. Miller

[57] ABSTRACT

A composition for the cosmetic treatment of human skin, particularly facial skin, to remove retention products from the skin surface and sebaceous follicles, is disclosed. The composition comprises a high-silica zeolite, the principal adsorbent constituent, dispersed in an aqueous medium using colloidal hectorite-type clays, a water soluble alkyl polyol preferably having from 2 to 6 hydroxyl groups, and most preferably a glycol such as propylene glycol, and an anti-microbial agent compatible with the high-silica zeolite.

7 Claims, No Drawings

FACIAL CLEANSING MINERAL COMPOSITIONS

FIELD OF THE INVENTION

The present invention relates in general to compositions useful in the cosmetic treatment of human skin, particularly facial skin, to cleanse the pores and remove retention products from the skin surface and sebaceous follicles. The composition contains as the principal adsorbent cleaning medium a mineral zeolite material, i.e., a high silica zeolite or polymorph, and is characterized by being highly effective in the absence of gums and/or mineral oils which are commonly used as essential ingredients in pore-cleaning cosmetic composition. The zeolitic adsorbent particles are dispersed in an aqueous medium by means of particular colloidal hectorite clays which do not require heating in aqueous media to induce functional swelling.

BACKGROUND OF THE INVENTION

The art and science of facial skin treatment to achieve and maintain a healthful condition and attractive appearance is very old and very comprehensive. The literature is replete with proposed treatments and compositions for that purpose which involve both physical and chemical approaches. In U.S. Pat. No. 4,752,472 (Kligman) a largely physical procedure is disclosed which comprises applying a layer of liquid polymerizable adhesive to the skin, then applying a pliable adhesive tape to cover the applied liquid adhesive and allowing the polymerization of the polymerizable adhesive to take place, followed by removing the layer of polymerized adhesive from the skin by stripping the tape from the skin. The materials on the surface of the skin and within the sebaceous follicles are thus attached to and removed along with the layer of polymerized adhesive and the tape.

By far the most common chemical treatment involves the use of soaps and detergent materials to render the natural oils and other biological materials secreted through the pores soluble or dispersable in water. These soaps or detergents are frequently combined with mildly abrasive materials, such as oat flour, or are used in conjunction with pads which comprise or contain abrasive substances such as disclosed in U.S. Pat. No. 4,769,022.

A third general type of skin cleansing is also quite old in the art and involves the use of materials such as clays, activated carbons and the like which are applied to the skin surface as a flowable dispersion or paste and allowed to dry to form what is commonly called a mask. In the dried state the mask composition acts as an absorbent for the surface and sebaceous oils. Upon removal of the mask, the undesirable retention products of the skin and pores are also removed. Such topical dermatological compositions, particularly those containing calcium sulfate, are disclosed in Bich N. Le U.S. Pat. No. 4,735,802, issued Apr. 5, 1988.

It is generally the case that the prior-proposed compositions which are utilized in the form of dry-hardened facial masks have one or more troublesome properties either from an aesthetic or functional standpoint. Many which contain clays, either alone or in combination with activated carbon, are dark, even black, in color and elaborate care must be exercised in their application and removal to avoid contact with and staining of clothing, toweling, linens or the like usually present at the site of the skin treatment or employed directly in carrying out the treatment. In many instances it is found necessary to include mineral oil and/or xantham gums to ameliorate the harsh properties of the dried mask composition. These additives are somewhat counterproductive in that they tend to be comedogenic and contribute to the clogged-pore condition sought to be remedied. Further, most of the organic constituents of the prior-proposed mask composition have distinct and often unpleasant chemical odors which must be endured by the person undergoing the treatment either as such or combined with a strong odor-masking fragrance.

SUMMARY OF THE INVENTION

There has now been discovered an improved cosmetic composition particularly useful as a cosmetic facial mask which comprises a high-silica zeolite dispersed in an aqueous hydrophilic colloid system consisting essentially of water and a colloidal sodium lithium magnesium silicate of the hectorite type, an antimicrobial preservative agent which retains activity in contact with high-silica zeolites, and a water-soluble alkyl polyol rheological modifier. This composition is odorless, has a white to off-white color, is highly effective in adsorbing oils and other organic retention products from the pores and surface of the skin, does not cause excessive extraction of water from the skin even after prolonged contact therewith, contains no gums, oils or other comedogenic substances and even in the dried state is easily rinsed completely from the skin. The present invention includes the process for treating the skin with the aforementioned cosmetic composition.

DETAILED DESCRIPTION OF THE INVENTION

The principal active ingredient of the compositions of the present invention is the high-silica zeolite, which is present in an amount of from about 30 to about 40 parts by weight (anhydrous basis). These high-silica zeolites are the hydrophobic crystalline siliceous microporous molecular sieves in which at least about 90, and preferably at least 95, per cent of the framework tetrahedral oxide units are $SiO_2$ tetrahedra and which have a sorptive capacity for water at 25° C. and 4.6 torr of less than about 10 weight per cent, preferably less than about 6 weight per cent. In the case of aluminosilicate molecular sieves, the framework $SiO_2/Al_2O_3$ ratio is at least 18 and is preferably at least 35. Molecular sieve zeolites having framework molar $Si/Al_2$ ratios of from 200 to 500 are particularly suitable. Many of the synthetic zeolites prepared using organic templating agents are readily produced in a highly siliceous form. In many instances the reaction mixtures can be especially free of aluminum-containing reagents. These zeolites are markedly organophilic and include ZSM-5 (U.S. Pat. No. 3,702,886); ZSM-11 (U.S. Pat. No. 3,709,979); ZSM-35 (U.S. Pat. No. 4,016,245); ZSM-23 (U.S. Pat. No. 4,076,842); and ZSM-38 (U.S. Pat. No. 4,046,859) to name only a few. It has been found that the silica molecular sieves known as silicalite and F-silicalite are particularly suitable for use in the present invention and are thus preferred. These materials are disclosed in U.S. Pat. No(s). 4,061,724 and 4,073,865, respectively. To the extent the aforesaid siliceous molecular sieves are synthesized to have $SiO_2/Al_2O_3$ ratios greater than 35, they are suitable for use in the present compositions without any additional treatment to increase their degree of hydrophobicity. Molecular sieves which cannot be directly synthesized to have both sufficiently high Si/Al and/or degree of hydrophobicity ratios can be subjected to dealumination techniques, fluorine treatments and the like, which result in organophilic zeolite products. High-temperature steaming procedures for treating zeolite Y which result in hydrophobic product forms are reported by P. K. Maher et al, "Molecular Sieve zeolites," Advan. Chem. Ser. 101, American Chemical Society, Washington, D. C., 1971, p. 266. A more recently reported procedure applicable to zeolite species generally involves dealumination and the substitution of silicon into the dealuminated lattice site. This process is disclosed in Skeels et al. U.S. Pat. No. 4,503,023, issued Mar. 5, 1985. Halogen or halide compound treatments for zeolites to increase their hydrophobicity are disclosed in U.S. Pat. No(s). 4,569,833 and 4,297,335.

In the case of the aluminosilicates or silica polymorphs produced using large organic templating ions, such as tetraalkylammoniun ions, it is frequently necessary to remove charge-balancing organic ions and any occluded templating material in order to permit their use in adsorption processes.

It should be pointed out that with respect to the hydrophobic aluminosilicates it is the framework $SiO_2/Al_2O_3$ ratio which is important. This is not necessarily the same ratio as would be indicated by conventional wet chemical analysis. Especially is this the case when dealumination has been accomplished by high temperature steaming treatments wherein aluminum-containing tetrahedral units of the zeolite are destroyed, but the aluminum values remain, at least in part, in the zeolite crystals. For such zeolite products resort must be had to other analytical methods such as X-ray and NMR. One such steam-treated zeolite Y composition, known in the art as LZ-10, has been found to be particularly useful in the compositions of the present process, especially when utilized in combination with the silica polymorph silicalite. The process for preparing LZ-10 is described in detail in U.S. Pat. No. 4,331,694 and in U.S. application Ser. No. 880,561, filed Feb. 23, 1978, now abandoned.

The aforesaid high-silica zeolites preferentially adsorb relatively non-polar organic molecular species rather than the highly polar water molecules. Thus, in the present compositions, these adsorbents are highly effective in adsorbing and retaining oils and other natural organic retention products and do not strongly extract water molecules from the skin. These zeolites are also uniquely effective in eliminating odors produced by the organic constituents of the cleansing composition and thereby avoid the discomforts caused by having to inhale such odors during the treatment period. Moreover, it is not necessary to mask the objectionable organic odors with strong fragrances which in themselves can be noisome to the user. The fact that the zeolite crystals are essentially white in color is a significant benefit over activated carbon absorbers used in certain of the prior proposed facial mask compositions.

As synthesized the molecular sieve particles have, in general, sizes of about 1.5 to about 6.0 micrometers. The particles are most frequently agglomerates having sizes in the range of 10 to about 20 micrometers. Molecular sieve particles in this range, i.e., 10 to 20 micrometers, are all suitably utilized in forming the present compositions. It is preferred, however, that the particles are within the size range of 1.5 to 6.0 micrometers. If it is necessary to reduce the molecular sieve particle size, the grinding techniques well known in the art are suitably employed.

As applied to the skin, the zeolite particles are dispersed in an aqueous matrix. The water is present in an amount of at least 45 parts by weight, and preferably from about 55 to 65 parts by weight in the as-prepared composition. The dispersion is maintained by the creation of a hydrophilic colloid system using from about 0.5 to 2.0 weight percent of a synthetic colloidal sodium lithium magnesium silicate having the hectorite or macaloid clay structure. This silicate contains exchangeable lithium and sodium cations instead of the aluminum cations present in natural magnesium silicates of the natural smectite clays sometimes employed as dispersing agents. These hectorite-type synthetic clays are commonly referred to as laponites and are widely available commercially. Various grades of available laponites exhibit different dispersion characteristics which can be used to prepare dispersions of various thicknesses, as desired. It has been found that in preparing the present compositions, a mixture of about 1.0 wt. % laponite XLG, characterized as producing fast dispersion, and about 0.5 wt. % laponite XLS, producing a slow dispersion, based on the weight of liquid water present, created a final composition of a highly satisfactory consistency for purposes of handling and application.

The alkyl polyol rheological modifier employed provides a cosmetic functionality and provides skin softening and conditioning. In the overall composition it is present in an amount of from about 2 to about 10 parts by weight. Advantageously the polyol employed is water-soluble to the extent that it forms a single liquid phase with the water present, and contains from 2 to 6 hydroxyl groups. The preferred polyols are the alkylene glycols such as hexylene glycol and 1,3-butylene glycol. A particularly preferred glycol is propylene glycol. Sorbitol, a hexahydric alcohol, is representative of other polyols suitably utilized.

The last essential ingredient of the composition is an antimicrobial or preservative agent which is compatible with, i.e., remains biologically active in the presence of the high-silica molecular sieve constituent. It is essential to prevent the growth of fungi, bacteria, molds viruses and the like in the composition during preapplication storage. The biocidally active constituent of the present invention must, therefore, be capable of retaining its activity over prolonged periods of time in contact with the zeolite constituent of the composition. It is found that many of the preservatives commonly employed in cosmetic compositions are not effective in the compositions of the present invention. Without wanting to be bound by any particular theory, it is believed that this ineffectiveness is due, at least in part, to these substances being adsorbed into the internal pore system of the zeolite crystals and are thus limited in their contact with microorganisms present in the medium outside the zeolite particles. It has been found that 5-chloro-2-methyl-4-isothiazolin-3-one (commercially available from Rohm & Haas Co. under the tradename KATHON-GC) and glutaraldehyde (commercially available from Union Carbide Chemicals and Plastics Co. under the tradename UCARCIDE) are examples of biocides which are effectively adsorbed by zeolites having medium to large pores and hence are not effective in the present compositions.

For the foregoing reasons, it is highly preferred to utilize as the biocidally active component a phenoxarsine-containing compound, preferably one that is soluble at least to a moderate extent in the glycol or aqueous media of the composition. Such compounds are well known in the art and include 10-chlorophenoxarsine; 10-bromophenoxarsine; 10-phenoxarsinyltrichloroacetate; (10-phenylarsinyl)-n-octylxanthate; 10-methylphenoxarsine; 10-butylphenoxarsine; 10-phenylphenyloxarsine; (10-phenoxarsinyl) diisopropylphosphonate; and 10,10'-oxybisphenoxarsine. A particularly preferred phenoxarsine compound for use in the present compositions is cis-1-(3-chloro-2-propanyl)-3,5,7-triaza-1-azoniatricyclo (3.3.1.1[3,7]) decane halide, particularly the chloride or bromide, available commercially under the trade name Dowicil 200, or as quaternium-15. The quantity of the biocide used is not critical, but should be present in an amount effective to prevent the growth of microorganisms, usually about 0.1 to 0.2 parts by weight.

While additional ingredients can be incorporated, such materials are either unnecessary or redundant. The simplicity of the present composition, insofar as the number of essential ingredients is concerned, is a major advantage. There is, for example, no need to employ odor-masking agents such as pentadecalactone since the high-silica zeolites are effective odor eliminators. Gums and oils as emollients and thickeners are replaced in function by the laponite ingredients, and in the absence of oils, no emulsifiers such as triethanolamine are required. Fragrances are both unnecessary and ineffective in the presence of the zeolite constituent. While colorants may be aesthetically desirable, in certain instances, the normal off-white color of the composition in the absence of added colorants is entirely acceptable as is.

In preparing the compositions of the present invention the order of mixing is not critical but advantageously the colloidal magnesium silica clay constituent is dispersed in the water at ambient room temperature using mechanical (propeller) agitation until the silicate has fully swelled and a hydrated suspension is obtained, usually about 30 minutes. Thereafter about one half of the high-silica zeolite constituent is added and blended to form a smooth dispersion. The polyol is then added to maintain the smoothness of the dispersion while the remaining zeolite is added. The biocide preservative is then added and blended to uniformly disperse it throughout the mixture.

In applying the composition to the skin, the conventional techniques are employed and the composition is permitted to dry and remain on the skin usually for periods of about 15 to 20 minutes, and then removed by rinsing with water. The preparation and use of a particular embodiment of the compositions of the present invention are illustrated by the procedures of the following Examples:

EXAMPLE 1 a) A cosmetic mask composition was prepared by adding 1.0 grams of laponite XLG and 0.5 grams of laponite XLS to 53.3 grams of distilled water at ambient room temperature, about 23° C. The mixture was agitated by stirring for a period of about 30 minutes until full swelling of the laponites had occurred. Thereafter 40 grams of silicalite, a silica polymorph having a framework $Si/Al_2$ ratio in excess of 180, along with 5.0 grams of propylene glycol were then added and the composition thoroughly blended. Finally 0.2 gram of Dowicil 200 was added and blended.

b) The efficacy of the composition of part (a) above as a pre-cleansing facial mask was tested and compared with a commercially available mask composition said to contain the following ingredients: infusions of melilot and equisteum arvenoc, kaolin (natural clay) polysorbate 20, bentonite, magnesium aluminum silicate, butylene glycol, peg-100 stearate, glycerin, activated charcoal, natural xanthan gum, lecithin, sorbitan laurate, propylene glycol stearate, propylene glycol, simethicone, dehydroacetic acid, methyl and propylparaben, imidazolidinyl urea, iron oxides, peg-150 distearate and trisodium EDTA.

After application and hardening of the mask compositions, a pleasant cooling effect on the skin was noticeable in the case of the composition of the present invention, an effect not provided by the comparison composition. The rinseability of present composition at the end of the treatment was excellent and superior to that of the comparison formulation, the latter being essentially black in color. After removal of the masks, the skin was soft and smooth in both treatments, but more so in the case of the treatment with the composition of the present invention.

EXAMPLES 2-7 a) Using the same ingredients as in Example 1, four additional compositions were formulated using different proportions of water, silicalite and propylene glycol as set forth in tabular form below:

| Ingredient | Example 2 | Example 3 | Example 4 | Example 5 |
|---|---|---|---|---|
| Laponite XLG | 1.0 wt. % | 1.0 wt. % | 1.0 wt. % | 1.0 wt. % |
| Lamponite XLS | 0.5 wt. % | 0.5 wt. % | 0.5 wt. % | 0.5 wt. % |
| Distilled $H_2O$ | 73.3 wt. % | 63.3 wt. % | 56.3 wt. % | 48.3 wt. % |
| Silicalite | 20.0 wt. % | 30.0 wt. % | 40.0 wt. % | 40.0 wt. % |
| Propylene Glycol | 5.0 wt. % | 5.0 wt. % | 2.0 wt. % | 10.0 wt. % |
| Dowicil 200 | 0.2 wt. % | 0.2 wt. % | 0.2 wt. % | 0.2 wt. % |

The composition of Example 2, which contained a low ratio of laponite to water and a high ratio of water to zeolite was found to separate to an undesirable degree. The other compositions were acceptable. The proportion of the composition of Example 3 was less viscous but smoother than the composition of Example 1. The composition of Example 4 was quite thick but remained workable. The composition of Example 5 was very similar to that of Example 1.

b) Using the same ingredients as in Example 1 except that sorbitol was substituted for propylene glycol, the following compositions were formulated:

| Ingredient | Example 6 | Example 7 |
|---|---|---|
| Laponite XLG | 1.0 wt. % | 1.0 wt. % |
| Laponite XLS | 0.5 wt. % | 0.5 wt. % |
| Distilled $H_2O$ | 53.3 wt. % | 48.3 wt. % |
| Silicalite | 40.0 wt. % | 40.0 wt. % |
| Sorbitol (70% solution) | 5.0 wt. % | 10.0 wt. % |
| Dowicil 200 | 0.2 wt. % | 0.2 wt. % |

Both of these compositions were acceptable but were generally thicker than corresponding compositions formulated with propylene glycol rather than sorbitol.

What is claimed is:

1. A composition useful as a cosmetic pore-cleansing facial mask which comprises a high-silica zeolite wherein the framework $SiO_2/Al_2O_3$ ratio is at least 18 dispersed in an aqueous colloidal system consisting essentially of water and a colloidal sodium lithium magnesium silicate having the crystal structure of hectorite, a phenoxarsine-containing compound as a biocidally active preservative agent which retains its biocidal activity in contact with the said high-silica zeolite, and an alkyl polyol rheological modifier; said high silica zeolite having at least 90 percent of its framework tetrahedral oxide units as $SiO_2$ tetrahedra and being present in an amount of 30 to 40 parts by weight; said liquid water being present in an amount of from 45 to 65 parts by weight; said colloidal sodium lithium magnesium silicate being present in an amount of from 0.5 to 2.0 weight percent; said alkyl polyol rheological modifier being present in an amount of 2 to 10 parts by weight; and said biocidally active preservative being present in an amount to effectively inhibit the growth of microorganisms in the overall composition.

2. Composition according to claim 1 wherein the alkyl polyol is water-soluble and contains from 2 to 6 hydroxyl groups.

3. Composition according to claim 2 wherein the alkyl polyol is a glycol.

4. Composition according to claim 3 wherein the colloidal magnesium silicate is a mixture of Laponite XLG and Laponite XLS.

5. Composition according to claim 3 wherein the glycol is a compound selected from the group consisting of propylene glycol, hexylene glycol and 1,3-butylene glycol.

6. Composition according to claim 1 wherein the phenoxarsine-containing compound is cis-1-(3-chloro-2-propanyl)-3,5,7-triaza-1-azoniatricyclo (3.3.1.1[3,7]) decane halide.

7. Process for treating the human skin to remove retention products from the skin surface and sebaceous follicles which comprises applying thereto a cosmetic composition according to claim 1, permitting said composition to dry and harden, and thereafter rinsing said dried composition from the skin surface.

* * * * *